US009592146B1

(12) United States Patent
DiNatale, Jr.

(10) Patent No.: US 9,592,146 B1
(45) Date of Patent: Mar. 14, 2017

(54) COLLAPSIBLE BONDAGE RACK

(71) Applicant: Charles DiNatale, Jr., Westminster, MA (US)

(72) Inventor: Charles DiNatale, Jr., Westminster, MA (US)

( * ) Notice: Subject to any disclaimer, the term of this patent is extended or adjusted under 35 U.S.C. 154(b) by 224 days.

(21) Appl. No.: 14/247,461

(22) Filed: Apr. 8, 2014

Related U.S. Application Data (60) Provisional application No. 61/810,300, filed on Apr. 10, 2013.

(51) Int. Cl.
*A61F 5/37* (2006.01)
*A47C 15/00* (2006.01)

(52) U.S. Cl.
CPC .......... *A61F 5/3761* (2013.01); *A47C 15/008* (2013.01)

(58) Field of Classification Search
CPC ......... A47C 15/008; A47C 4/00; A47C 4/286; A47G 25/0664; A61F 5/37; A61F 5/3761; A61F 5/3769
USPC ...... 128/845, 869, 870, 883; 297/16.1, 16.2, 297/42, 51–54; 600/38; 5/627, 628; 601/23, 24; 482/142–144; 211/1, 189, 211/195, 198–200, 203
See application file for complete search history.

(56) References Cited

U.S. PATENT DOCUMENTS

| | | | |
|---|---|---|---|
| 552,956 A * | 1/1896 | Foisy | A47C 9/00 108/128 |
| 2,834,644 A | 5/1958 | Johansson et al. | |
| 3,971,592 A | 7/1976 | Farley | |
| 4,099,773 A | 7/1978 | Chang | |
| 4,373,222 A | 2/1983 | Wolfe et al. | |
| 4,825,855 A | 5/1989 | Kundson, Jr. | |
| 5,385,154 A | 1/1995 | Fuhrman et al. | |
| 5,443,532 A | 8/1995 | Hudak | |
| 5,453,080 A | 9/1995 | Mitchum, Jr. | |
| 5,470,039 A | 11/1995 | Hilger | |
| 5,538,011 A | 7/1996 | Craft et al. | |
| 5,586,560 A | 12/1996 | Boutos | |
| 5,875,779 A | 3/1999 | Fuhrman et al. | |
| 6,030,039 A | 2/2000 | Essler | |
| 6,338,344 B1 | 1/2002 | Sinohui, Jr. | |
| 6,817,671 B1 | 11/2004 | Zheng | |
| 6,871,905 B2 * | 3/2005 | Grace | A47C 9/105 297/16.2 |

(Continued)

*Primary Examiner* — Keri J Nelson
(74) *Attorney, Agent, or Firm* — Thomas P. O'Connell; O'Connell Law Firm (57) ABSTRACT

A collapsible bondage rack with use and collapsed configurations. An upper retaining structure, potentially formed by upper legs disposed in a V-configuration, and a lower support structure, potentially formed by anterior and posterior lower legs, each disposed in a V-configuration, are retained relative to a main hinge assembly. The upper retaining structure and the lower support structure are relatively pivotable between use and collapsed configurations. The anterior and posterior lower legs are pivotable about a lateral pivot axis between use and storage configurations, and the anterior lower legs are pivotable about a longitudinal pivot axis. The legs are disposed in a stack when the bondage rack is collapsed. Foot mount assemblies are retained by the anterior lower legs, and attachment assemblies are retained by the upper legs and the anterior lower legs. Leveling mechanisms can stabilize the bondage rack.

22 Claims, 5 Drawing Sheets

(56) References Cited

U.S. PATENT DOCUMENTS

| | | |
|---|---|---|
| 6,991,599 B2 | 1/2006 | Hudson |
| 7,340,789 B2 | 3/2008 | Cloward |
| 2009/0174233 A1 * | 7/2009 | Hoffman ................ A47C 4/286 297/16.2 |
| 2009/0285948 A1 | 11/2009 | Tucker |

* cited by examiner

COLLAPSIBLE BONDAGE RACK

RELATED APPLICATION

This application claims priority to U.S. Provisional Patent Application No. 61/810,300, filed Apr. 10, 2013, which is incorporated herein by reference.

FIELD OF THE INVENTION

The present invention relates generally to support structures. More particularly, disclosed and protected herein is a collapsible rack capable of supporting and, where applicable, permitting a restraint of an occupant whereby the collapsible rack functions as a portable and novelty bondage rack.

BACKGROUND OF THE INVENTION

Numerous bondage racks have been disclosed by the prior art. Unfortunately, currently disclosed bondage racks suffer from a number of limitations and disadvantages. For instance, existing bondage racks typically do not even attempt to permit portability. Accordingly, few bondage racks are designed to collapse or fold to permit storage or transport. Those that are designed to break down have many separate pieces, are heavy, and require tools and considerable time to manipulate between a use configuration and a collapsed configuration. Moreover, in their stored state, such racks occupy a large area. Still further, even bondage racks that attempt to provide portability are not easily packed in storage and transport containers and normally do not come with any means for permitting storage. Consequently, their portability and ease of storage are further limited as is the discretion of one seeking to store and transport the bondage rack.

It will be further noted that most bondage racks of the prior art are not freestanding. Consequently, they commonly require mounting or leaning onto a wall for stability. Moreover, bondage racks of the prior art commonly lack leveling features to account for uneven surfaces during use whereby stability may be compromised. Further still, many bondage racks are unsound ergonomically. Among the negative results of poor ergonomic design is that users are forced to compensate for the angle between the rack and the floor, such as by bending at the ankle. This decreases the user's stability and increases the potential for the user's feet to slide.

The present inventor has thus recognized that it would be advantageous to provide a bondage rack that is collapsible to facilitate portability, storage, and discreteness. It is further recognized that a bondage rack that is ergonomically sound and capable of being stabilized on a support surface to permit effective use and operation of the rack would represent a useful advance in the art.

SUMMARY OF THE INVENTION

In view of the foregoing, the present inventor set forth with the basic object of providing a bondage rack that overcomes the foregoing and further disadvantages and limitations of prior art structures.

A more particular object of the invention is to provide a bondage rack that is collapsible, such as by folding, for portability, storage, and discreteness.

A further object of embodiments of the invention is to provide a bondage rack that is ergonomically sound to permit effective use and operation of the rack.

Another object of the invention in particular embodiments is to provide a portable bondage rack that can be stabilized on a support surface to provide stable and reliable use.

Yet another object of embodiments of the invention is to provide a portable bondage rack that can be stored and transported discretely, potentially in a dedicated storage container.

These and further objects and advantages of the present invention will become obvious in view of the present specification and drawings. However, it will be appreciated that, although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In carrying forth one more objects of the invention, an embodiment of the collapsible bondage rack has a use configuration and a collapsed configuration. The bondage rack has a main hinge assembly. An upper retaining structure is retained relative to the main hinge assembly, and a lower support structure is retained relative to the main hinge assembly. The upper retaining structure and the lower support structure are relatively pivotable by operation of the main hinge assembly between a use configuration and a collapsed configuration.

The upper retaining structure could, for example, comprise first and second upper legs and wherein the lower support structure comprises first and second lower legs. When the collapsible bondage rack is in a use configuration, the first and second legs of the upper retaining structure project from the main hinge assembly in a first longitudinal direction and the first and second legs of the lower support structure project from the main hinge assembly in a second longitudinal direction substantially opposite the first longitudinal direction. In particular manifestations of the invention, the first and second legs of the upper retaining structure project from the main hinge assembly in a substantially V-shaped configuration and the first and second legs of the lower support structure project from the main hinge assembly in a substantially V-shaped configuration when the collapsible bondage rack is in a use configuration.

The lower support structure could, for example, have an anterior lower support and a posterior lower support. The anterior lower support and the posterior support can have proximal end portions retained relative to the main hinge assembly, and the anterior lower support and the posterior lower support can be relatively pivotable between a use configuration wherein the anterior and posterior lower supports are spaced apart and a collapsed configuration wherein the anterior lower support and the posterior lower support are pivoted into proximity. In such embodiments, the upper retaining structure can be formed by first and second upper legs, the anterior lower support of the lower support structure can be formed by first and second anterior lower legs, and the posterior lower support of the lower support structure can comprise first and second posterior lower legs.

Pursuant to embodiments of the invention, the first and second upper legs, the first and second anterior lower legs, and the first and second posterior lower legs can be disposed in a stack configuration when the bondage rack is in the collapsed configuration. Moreover, the first and second legs of the upper retaining structure can be pivotable about a lateral pivot axis relative to the first and second anterior lower legs, and the first and second posterior lower legs can be pivotable about a lateral pivot axis relative to the first and second anterior lower legs. Still further, it is contemplated that the first anterior lower leg can be pivotable relative to the second anterior lower leg about a longitudinal pivot axis of the bondage rack thereby to facilitate the stacking collapsed configuration.

Where the upper retaining structure and the lower support structure are relatively pivotable about a lateral pivot axis, the lateral pivot axis could be formed with a structural link that has a first end pivotally coupled to a hinge base of the main hinge assembly and a second end pivotally coupled to a proximal portion of the upper retaining structure. Under such constructions, the main hinge assembly can further comprise a backing wall with the tongue and thus the structural link being limited in rotation by the backing wall when the bondage rack is in the use configuration. Still further, a locking mechanism, such as one or more locking screws, can be adjustable to fix the upper retaining structure against pivoting relative to the lower support structure and to permit the upper retaining structure to pivot relative to the lower support structure.

The bondage rack can additionally include first and second foot mount assemblies that can be retained in proximity to a distal end of the lower support structure, such as adjacent to the first and second anterior lower legs. By way of example, each of the first and second foot mount assemblies could comprise an aperture in the lower support structure. The foot mount assemblies could further include at least one foot plate and potentially an anterior foot plate and a posterior foot plate. Furthermore, first and second upper attachment assemblies, such as but not limited to loops, could be retained by the upper retaining structure and first and second lower attachment assemblies could be retained by the lower support structure. The first and second lower attachment assemblies could be disposed proximal to the first and second foot mount assemblies. Even further, leveling mechanisms, such as screws rotatable by operation of thumb dials, could be coupled to the first and second anterior lower legs for permitting a stabilization of the bondage rack.

One will appreciate that the foregoing discussion broadly outlines the more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention.

DETAILED DESCRIPTION OF PREFERRED EMBODIMENTS

The collapsible bondage rack disclosed herein is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

Figure 1A:
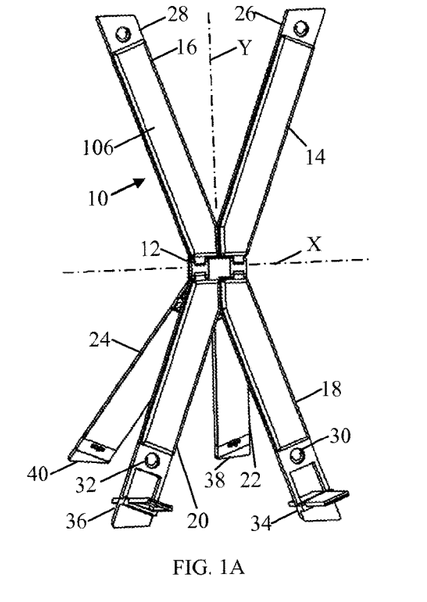
FIG. 1A is a front perspective view of the collapsible, portable bondage rack in a use configuration.
Figure 1B:
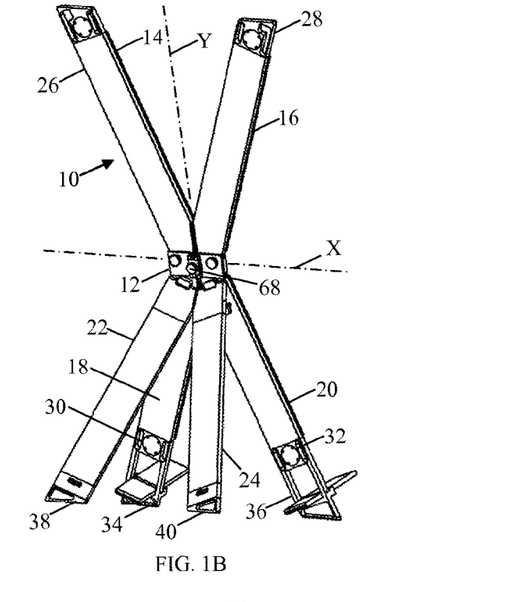
FIG. 1B is a rear perspective view of the collapsible, portable bondage rack in a use configuration.

Turning more particularly to the drawings, a collapsible bondage rack according to the present invention is indicated generally at 10 in FIGS. 1A and 1B where the bondage rack 10 is depicted in a use configuration. The illustrated embodiment of the bondage rack 10, which is merely exemplary, can be considered to be founded on a main hinge assembly 12. An upper retaining structure, discussed further hereinbelow, projects from the main hinge assembly 12 in a first longitudinal direction, and a lower support structure, also discussed further hereinbelow, projects from the main hinge assembly 12 in a second longitudinal direction opposite the first.

The upper retaining structure in this embodiment is formed by first and second upper legs 14 and 16 that project from the main hinge assembly 12. Here, the upper legs 14 and 16 project in a V-configuration, but the invention is not so limited. When the bondage rack 10 is in the use configuration standing upright on a support surface as illustrated, the upper retaining structure formed by the legs 14 and 16 projects upwardly from and above the main hinge assembly 12.

The lower support structure in this embodiment is formed by first and second anterior lower 18 and 20 that project from the main hinge assembly 12 to form an anterior lower support, potentially together with first and second posterior lower legs 22 and 24 that form a posterior lower support. The anterior lower legs 18 and 20 project in an upside-down V-configuration as do the posterior lower legs 22 and 24. Under this construction, the upper legs 14 and 16 forming the upper retaining structure and the anterior lower legs 18 and 20 are disposed essentially in an X-configuration when the bondage rack 10 is in a use configuration.

Moreover, when the bondage rack 10 is fully disposed in a use configuration as illustrated, the posterior lower legs 22 and 24 and the anterior legs 18 and 20 are disposed with an angle therebetween. With this, a V-shape is disposed between the first anterior lower leg 18 and the first posterior lower leg 22, and a V-shape is disposed between the second anterior lower leg 20 and the second posterior lower leg 24. Of course, it will again be appreciated that the invention is not so limited. When the bondage rack 10 is in the use configuration standing upright on a support surface as illustrated, the lower support structure formed by the anterior lower legs 18 and 20 and the posterior lower legs 22 and 24 projects downwardly from and below the main hinge assembly 12. Together, the legs 18, 20, 22, and 24 form a stable, four-point support for the bondage rack 10.

Figure 3A:
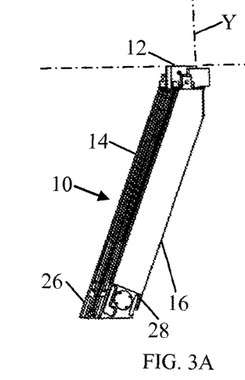
FIGS. 3A and 3B are perspective views of the collapsible, portable bondage rack in a collapsed configuration.
Figure 3B:
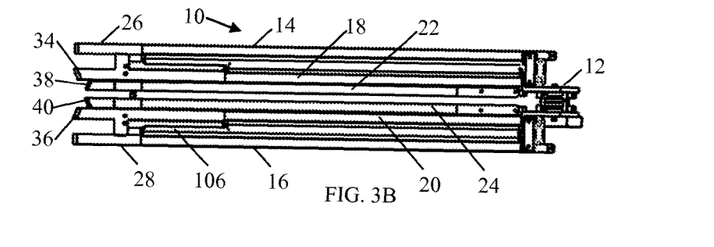
Figures 4, 5:
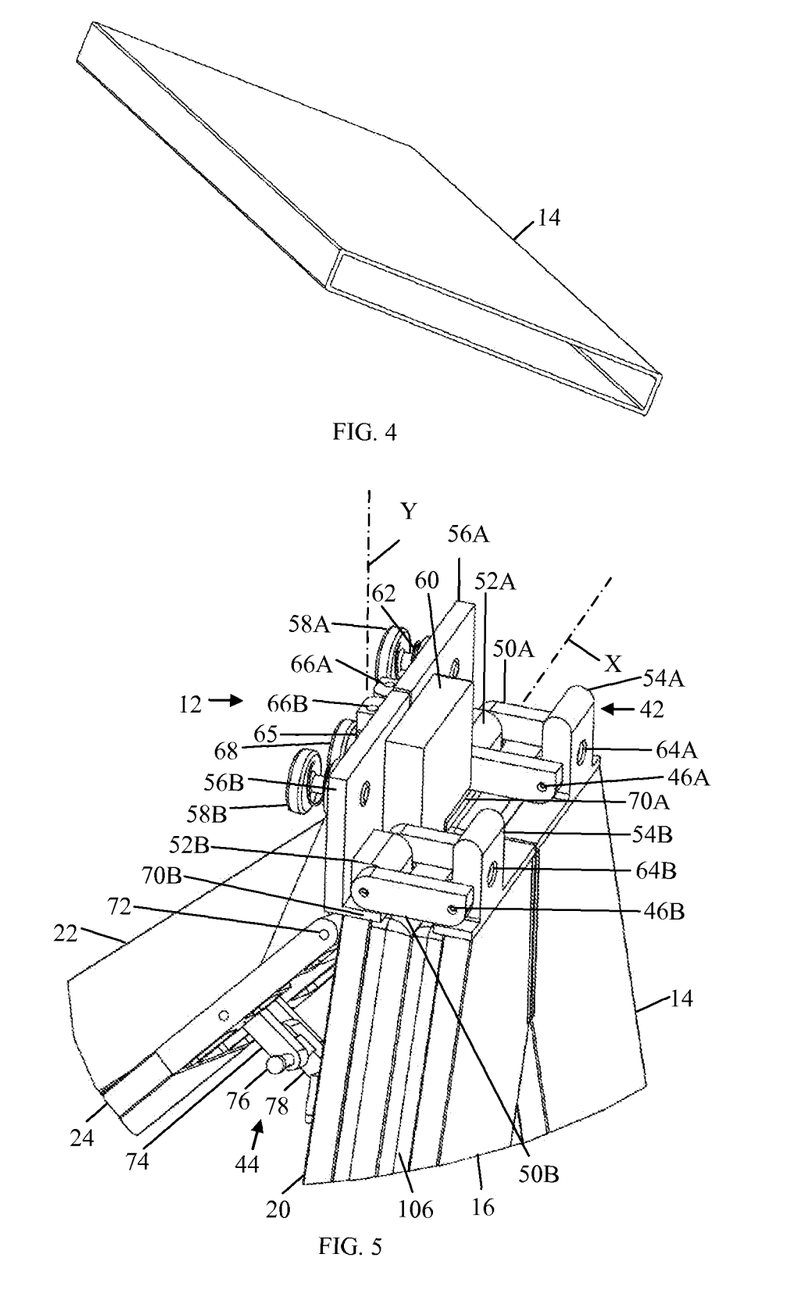
FIG. 4 is a perspective view of a portion of a structural frame member for the collapsible, portable bondage rack.
FIG. 5 is an amplified front perspective view of a main hinge assembly of the collapsible, portable bondage rack folded along the horizontal axis.

As seen, for example, in FIG. 5, the main hinge assembly 12 has a upper hinge assembly 42 and a rear hinge assembly 44. The upper hinge assembly 42 folds on two axes: one lateral and one longitudinal. The rear hinge assembly 44 folds on one axis. By use of the hinges 42 and 44, the legs 18, 20, 22, and 24 and the bondage rack 10 in general can be adjusted from the use configuration depicted in FIGS. 1A and 1B to the storage configuration depicted in FIGS. 3A and 3B where all of the legs 14, 16, 18, 20, 22, and 24 are disposed in a stack configuration. FIGS. 2A through 2E show the collapsible bondage rack 10 in stages of adjustment from the use configuration to the collapsed configuration. The range of kinematic motion of the legs 14, 16, 18, 20, 22, and 24 is controlled by the hinge assemblies 42 and 44 to allow manipulation between the use and storage configurations.

The depicted embodiment of the upper hinge assembly 42 provides angular kinematic motion along or at least partially aligned with a lateral pivot axis X and along or at least partially aligned with a longitudinal pivot axis Y. As used herein, references to pivoting or rotating about a given pivot axis shall include pivoting or rotating directly about the referenced pivot axis and pivoting or rotating in parallel to or even in general or approximate alignment with the referenced pivot axis.

Figure 2A:
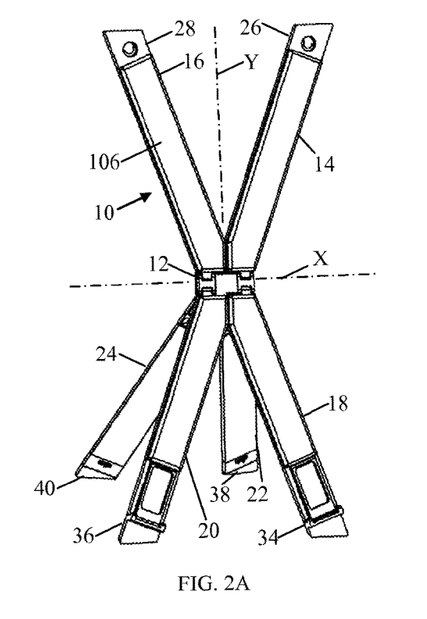
FIGS. 2A through 2E are perspective views of the collapsible, portable bondage rack in stages of adjustment from the use configuration to a collapsed configuration.
Figure 2B:
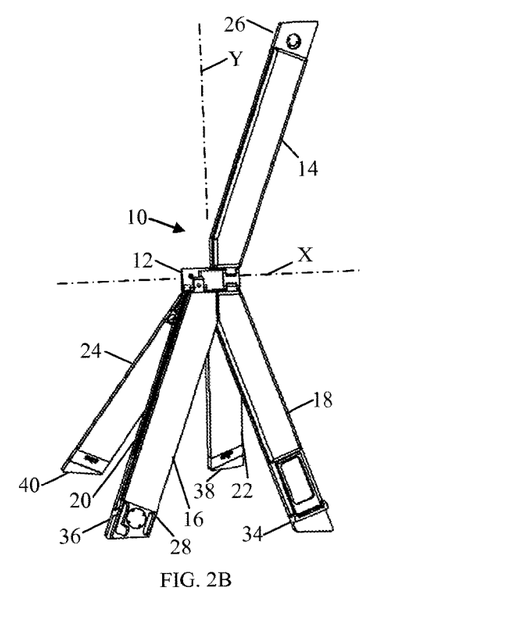
Figure 2C:
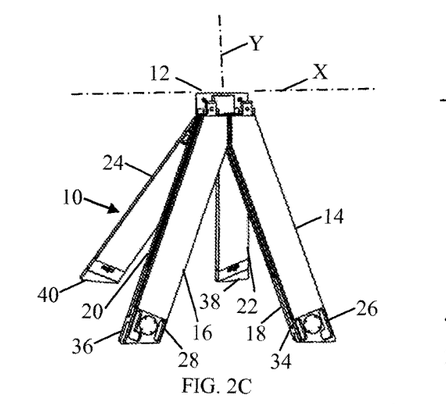
Figure 2D:
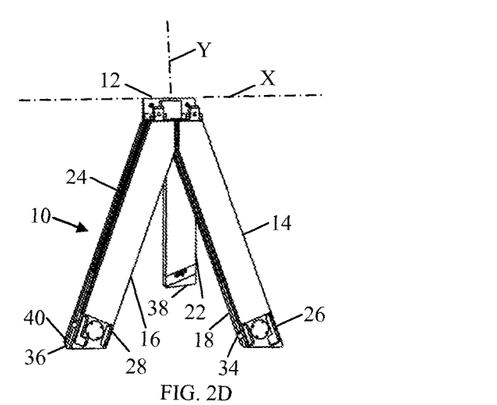

As suggested, for instance, by FIGS. 2A through 2C, the upper legs 14 and 16 can be folded about the lateral pivot axis X from the use configuration of FIG. 1A to a position in a facing relationship with the anterior lower legs 18 and 20. As a result, the distal ends of the legs 14 and 16 will be brought into proximity with the distal ends of the legs 18 and 20 as is illustrated, for example, in FIGS. 2C and 5. There is a lateral pivot axis 46A for the first upper leg 14 and a lateral pivot axis 46B for the second upper leg 16. Each of the lateral pivot axes 46A, 46B have two parallel main structural links 50A, 50B. The structural links 50A retaining the first upper leg 14 have a first end pivotally coupled to a first hinge base 52A and a second end pivotally coupled to a proximal portion of the leg 14. The structural links 50B retaining the second upper leg 16 have a first end pivotally coupled to a second hinge base 52B and a second end pivotally coupled to a proximal portion of the leg 16. With that, two lateral pivot axes are established for each leg 14 and 16. The proximal ends of the legs 14 and 16 have tongues 54A, 54B that extend between the structural links 50A, 50B.

The hinge bases 52A, 52B are respectively disposed in immediate proximity to first and second backing walls 56A, 56B and first and second base plates 70A, 70B. The first and second backing walls 56A, 56B and the first and second base plates 70A, 70B are fixed together, such as by being integrally formed. Under this construction, the first upper leg 14 and the first anterior lower leg 18 are effectively retained by the structure formed by the first backing wall 56A and the first base plate 70A, and the second upper leg 16 and the second anterior lower leg 20 are effectively retained by the structure formed by the second backing wall 56B and the second base plate 70B.

By the combined effects of the structural links 50A, 50B, the hinge bases 52A, 52B, the tongues 54A, 54B, the backing walls 56A, 56B, and their own construction, the legs 14 and 16 are automatically limited in kinematic motion to ensure proper operation and manipulation between use configuration and collapsed configuration. Stated alternatively, the legs 14 and 16 can be pivoted to the position shown in FIGS. 2C and 5 and limited against further pivoting by their contact with the legs 18 and 20. Moreover, when the legs 14 and 16 are pivoted to the use configuration of FIGS. 1A and 1B, the structural links 50A, 50B will be brought into longitudinal alignment with the tongues 54A, 54B and the legs 14 and 16 in general, and further pivoting will be prevented by the backing walls 56A, 56B. It is possible, but not required, for thrust bushings to be employed to limit translation and provide a low friction surface, and the structural links 50A, 50B can pivot on press fit spring pins.

When the legs 14 and 16 are pivoted to the use configuration of FIGS. 1A and 1B, the upper legs 14 and 16 can be secured in position, such as by bolts 58A, 58B respectively passed through the respective backing walls 56A, 56B and into threaded engagement with threaded apertures 64A, 64B in the respective tongue 54A, 54B or other portions of the legs 14 and 16. The bolts 58A, 58B can pass through the respective backing walls 56A, 56B and be captive therein, and the bolts 58A, 58B can be spring loaded with coil springs 62. The legs 14 and 16 are thus fixed to the backing walls 56A, 56B, and further angular travel of the legs 14 and 16 is thus limited by the tongues 54A, 54B and the backing walls 56A, 56B. Approximately 90 degrees of angular travel can be provided around each spring pin joint of the links 50A, 50B.

With the legs 14 and 16 folded to overlap the legs 18 and 20, the overlapping legs 14 and 18 can be pivoted about a longitudinal axis Y in relation to the overlapping legs 16 and 20, or vice versa, to render the bondage rack 10 still more compact in achieving the configuration of FIGS. 3A and 3B. When the bondage rack 10 is in the collapsed configuration in the present embodiment, the first and second upper legs 14 and 16, the first and second anterior lower legs 18 and 20, and the first and second posterior lower legs 22 and 24 are aligned and disposed in a stacked form as seen in FIGS. 3A and 3B.

The vertical or longitudinal hinge of the upper or main hinge assembly 12 could vary in construction within the scope of the invention. The vertical hinging arrangement could be similar in construction to the horizontal hinging of the first and second legs 14 and 16. In the depicted embodiment, a pivot link 65 is pivotally coupled to the first backing wall 56A by a first longitudinal pivot axis 66A and to the second backing wall 56B by a second longitudinal pivot axis 66B. With that, the overlapping legs 14 and 18 can be pivoted in relation to the overlapping legs 16 and 20 to be disposed in a facing and still more compact configuration as is illustrated, for example, in FIGS. 3A and 3B. The longitudinal pivot axes 66A, 66B could be formed by any effective pivotal coupling. In one instance, for example, the longitudinal pivot axes 66A, 66B can be formed from spring pins and thrust washers and can permit approximately ninety degrees of travel around each spring pin joint or longitudinal pivot axis 66A, 66B.

The longitudinal hinge could be locked against inadvertent pivoting in the use configuration of FIGS. 1A and 1B.

Numerous locking mechanisms are possible, each within the scope of the invention except as it might expressly be limited by the claims. In the illustrated embodiment as seen best in FIGS. 1B and 5, the locking mechanism comprises a threaded bolt 68 that passes through or between the backing walls 56A, 56B and into a threaded locking block 60 disposed to the opposite side of the backing walls 56A, 56B and is fixed to one or the other of the backing walls 56A, 56B, in this case the second backing wall 56B. With that, the legs 14, 16, 18, and 20 can be selectively locked against pivoting between an open or use configuration as in FIGS. 1A and 1B and a closed or collapsed configuration as in FIGS. 3A and 3B.

The threads of any or all of the tongues 54A, 54B and the block 60 can comprise thread inserts. For example, the threads could comprise precision formed screw thread coils of, for example, stainless steel wire, potentially with a diamond shape cross section. Such screw thread coils are, for instance, sold by Emhart Teknologies Inc. under the trademark HELI-COIL. Such thread inserts can provide a stronger fastened joint, particularly where the substrate is formed of a material designed for light weight and portability, such as aluminum. Embodiments of the rack 10 are contemplated where some or all components forming the hinges are formed from aluminum while other components requiring the strength, such as the threads, thread inserts, spring pins, thumbscrews, and thrust bushings, could be steel or a similarly strong and tough material.

Figure 2E:
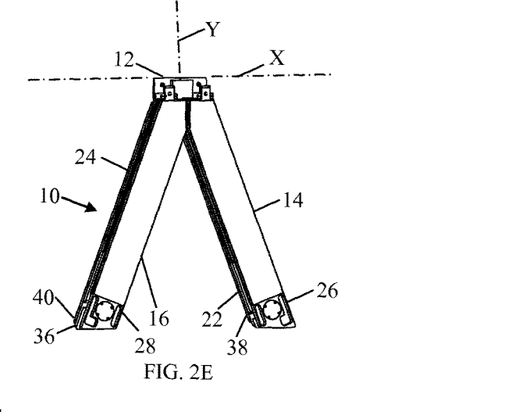

The posterior lower legs 22 and 24 can be pivoted from the use configuration depicted in FIGS. 1A through 2C and FIG. 5 to the collapsed configuration depicted, for instance, in FIGS. 2E, 3A, and 3B where the legs 22 and 24 are disposed in contact with the posterior faces of the anterior lower legs 18 and 20. By way of example and not limitation and with reference to the second posterior lower leg 24, the posterior lower legs 22 and 24 can be pivoted about essentially lateral pivot axes 72 disposed at the proximal ends of the legs 22 and 24. The legs 22 and 24 can be selectively locked in their use configuration by rear hinge assembly 44.

Figure 6A:
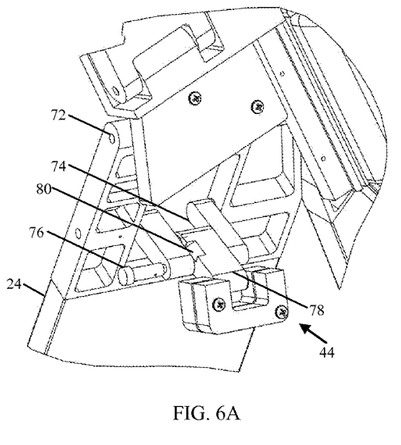
FIG. 6A is an amplified perspective view of a rear hinge assembly in a use configuration with the structural frame member and padding assembly removed for clarity of illustration.
Figure 6B:
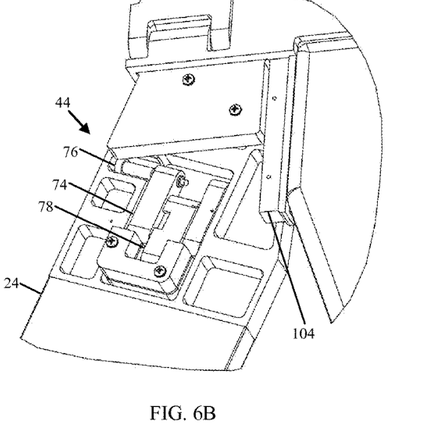
FIG. 6B is an amplified perspective view of the rear hinge assembly in a collapsed configuration, again with the structural frame member and padding assembly removed for clarity of illustration.

One of the many possible rear hinge assemblies 44 possible under the invention, is shown perhaps most clearly in FIGS. 6A and 6B where the rear hinge assemblies 44 are disposed in use and collapsed configurations respectively with the anterior lower leg 20 removed for clarity of illustration. The rear hinge assemblies 44 connect the posterior lower legs 22 and 24 to the anterior lower legs 18 and 20 at a distance spaced from the proximal ends thereof to provide a kinematic linkage system that defines the motion of the legs 22 and 24. A spring-loaded detent assembly 76 can automatically lock the legs 22 and 24 in the use configuration of FIG. 6A, and the legs 22 and 24 can be permitted to pivot to the collapsed configuration of FIG. 6B by a pulling on the detent assembly 76. A center link 78 of the rear hinge assembly 44 can have a lead-in feature 80 that compresses the spring detent assembly 76 before it occupies a slot feature as it attempts to pass, locking the assembly position. The spring detent assembly 76 can be seen to be formed in this embodiment by a spring detent top, a spring detent bottom, a dowel pin that is press fit to connect them and a coil spring. These components are assembled around the outer links 74 so that the spring detent assembly 76 is also captive hardware.

It will be appreciated that, within the scope of the invention, the legs 14, 16, 18, 20, 22, and 24 could be crafted from any suitable material and with any suitable physical construction. As is illustrated in FIG. 4, the legs 14, 16, 18, 20, 22, and 24 could in one example of the invention be formed of an extruded aluminum with a rectangular cross section. The legs 14, 16, 18, 20, 22, and 24 can be post-machined with a milling process. The legs 14, 16, 18, 20, 22, and 24 can be of similar or different lengths. The length of each legs 14, 16, 18, 20, 22, and 24 is machined to within tolerance, and features can be added to match the geometry of mating features on the main hinge assembly 12, such as overall shape and clearance holes for screws and spring pins.

Figures 7A, 7B:
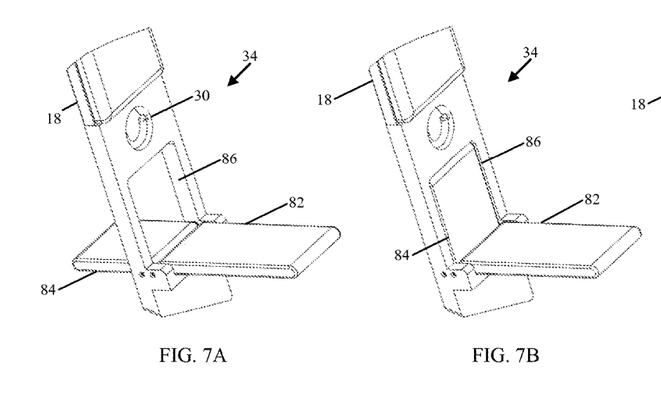
FIGS. 7A, 7B, and 7C are amplified perspective views of a foot mount assembly of the collapsible, portable bondage rack in use configuration, rear collapsed configuration, and rear and front collapsed configurations respectively.
Figure 7C:
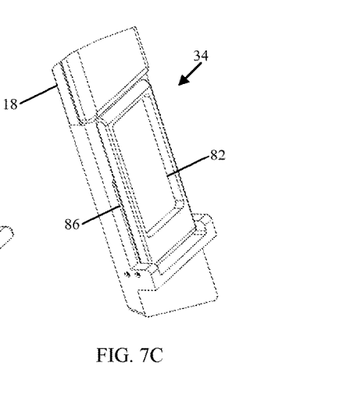

First and second foot mount assemblies 34 and 36 are retained in proximity to the distal or lower ends of the first and second lower anterior legs 18 and 20. The foot mount assemblies 34 and 36 provide ergonomic comfort for the user and contribute to the ability of the rack 10 to be freestanding and stable. In one embodiment as seen in FIG. 7A relative to the first foot mount assembly 34, the foot mount assemblies 34 and 36 include an aperture 86 through which a user's foot (not shown) can be received. The foot mount assemblies 34 and 36 further include anterior foot plate 82 and a posterior foot plate 84. The foot plates 82 and 84 could be pivotable, such as from a first, use position projecting outwardly from the respective leg 18 or 20 and a second, storage position substantially aligned with the respective leg 18 or 20. The first and second positions can be spaced, for example, by ninety degrees. The posterior foot plate 84 could, as shown, pivot to close the aperture 86 when in a storage position, and the anterior foot plate 82 could, as is also shown, pivot to overlie the aperture 86 and the lower attachment assemblies 30 and 32, which are discussed further hereinbelow. A person's foot can thus be received facing anteriorly or posteriorly and can be supported by the base of the aperture 86 and either or both foot mount assemblies 34 and 36. It will be noted that it could be possible to have a foot mount assembly 34 or 36 that simply has the aperture 86 or one or both of the anterior and posterior foot plates 82 or 84.

The distal ends of the lower legs 18, 20, 22, and 24 are disposed at mitered angles corresponding to the angles at which the legs 18, 20, 22, and 24 project away from vertical when the rack 10 is standing on a support surface with the four legs 18, 20, 22, and 24 as support. As a result, the ends of the legs 18, 20, 22, and 24 can rest flat on the support surface. The foot plates 82 and 84 can be disposed normal to the longitudinal of the legs 18 and 20 such that user can assume a natural ergonomic form and the potential of slippage between the user's feet and the plates 82 and 84 is greatly reduced. The length of the plates 82 and 84 and size of the aperture 86 also contribute to the ability of the user to face towards or away from the rack 10 as previously noted. The user's own weight increases the force between the rack 10 and the support surface which minimizes the effects of external forces while in use thus contributing to the freestanding stability of the rack 10. The foot plates 82 and 84 can also use spring pins and thrust bushings in the same manner as previous assemblies while the other materials in the assemblies of the foot plates 82 and 84 can be of any suitable material, such as aluminum.

Upper attachment assemblies 26 and 28 can be retained by the first and second upper legs 14 and 16 respectively, such as by being disposed adjacent to the distal ends thereof, and lower attachment assemblies 30 and 32 can be retained by the first and second anterior lower legs, such as by being disposed adjacent to the distal ends thereof. In this manifestation of the invention, the upper attachment assemblies 26 and 28 are in immediate proximity to the distal ends of the legs 14 and 16. The lower attachment assemblies are disposed proximal to the footplates 82 and 84 and the aperture 86 thereby facilitating retention of a user. The attachment assemblies 26, 28, 30, and 32 permit the attachment of external anchoring devices for the purpose of restraint thereby providing four dedicated points of restraint on the rack 10.

Figure 8A:
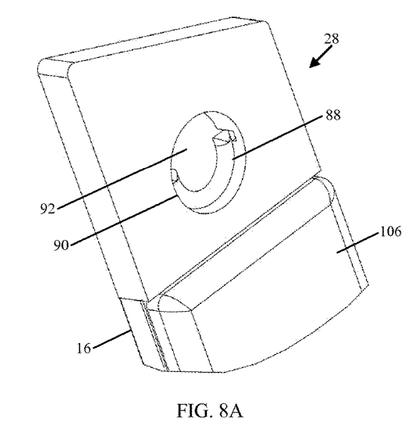
FIG. 8A is an amplified perspective view of an upper attachment assembly unoccupied and at rest position.
Figure 8B:
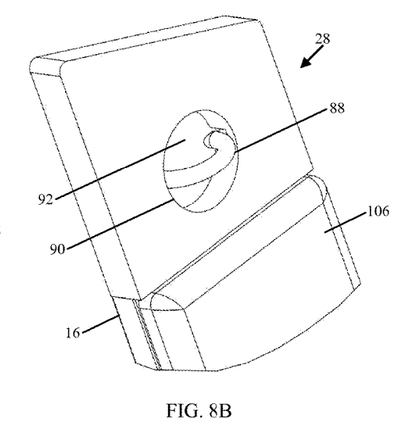
FIG. 8B is an amplified perspective view of the attachment assembly in a one possible use configuration pursuant to the invention taught herein.

The attachment assemblies 26, 28, 30, and 32 can vary in construction within the scope of the invention. The embodiment has attachment assemblies 26, 28, 30, and 32 with a semi-circular component 88, which may be referred to as a knocker loop 88, pivotably retained within an aperture 90 in the respective leg 14, 16, 18, and 20. The knocker loop 88 is pivotable over 180 degrees with a 90-degree pivoting illustrated in FIG. 8B in comparison to FIG. 8A. This allows the user to pass materials including, but not limited to, rope, chain and cloth inside the knocker loop 88 for fastening thereto. A backing plate 92 can be disposed behind the knocker loop 88. The backing plate 92 could have dowel pins or another mechanism to limit the translational movement of the knocker loop 88. The knocker loop 88 itself could be a one-piece sand casted or molded part. The materials could, for example, be aluminum or plastic except for the dowel pins and screws, such as those securing the backing plate 92.

One or more of the lower legs 18, 20, 22 and 24 could include a leveling mechanism, such as a mechanism for adjusting the effective length of the respective leg 18, 20, 22 and 24. The leveling mechanism or mechanisms can compensate for, among other things, an uneven surface under the rack 10. In the illustrated embodiment, leveling mechanisms 38 and 40 are disposed at the distal ends of the first and second posterior lower legs 22 and 24.

Figure 9A:
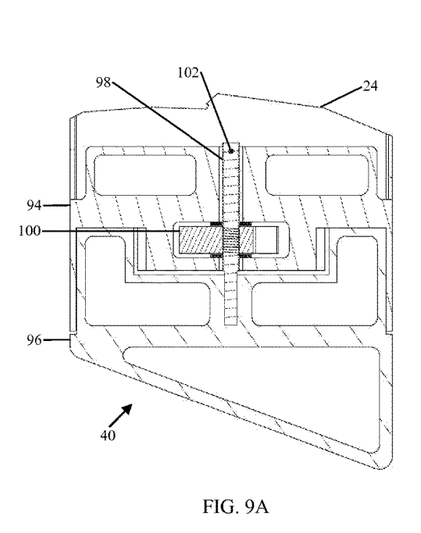
FIG. 9A is an amplified cross-sectional view of a leveler mechanism according to the invention in a retracted position.
Figure 9B:
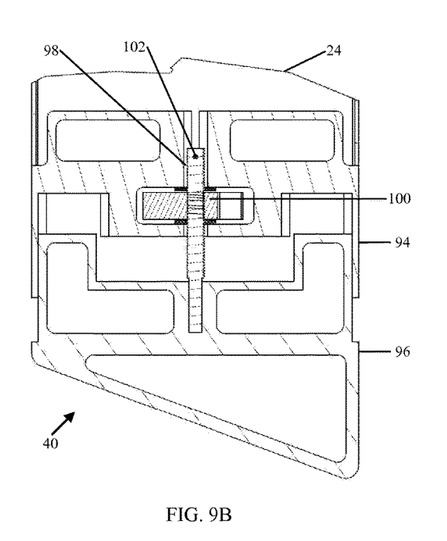
FIG. 9B is an amplified cross-sectional view of the leveler mechanism in an extended position.

The leveling mechanisms 38 and 40 can be manually or automatically adjusted between, for example, a retracted disposition as shown in FIG. 9A relative to the leveling mechanism 38 and an extended disposition as shown in FIG. 9B. In this embodiment, the mechanisms 38 and 40 have a leveler main body 94 that can be fixed to or be part of the respective leg 22 or 24 and an extendible leveling member 96. The leveling member 96, could, for example, translate within the leveler main body 94. The leveling member 96 could be adjusted between extended and retracted positions by a combination of the leveler screw 98 and an adjustment dial 100. The distance of travel of the leveling member 96 could vary within the scope of the invention. Overextension of the leveling member 96 can be limited, such as by a dowel pin 102 contacting the leveler main body 94. The leveler screw 98 could in one practice of the invention be press fit into the leveling member 96, threaded through the adjustment dial 100, and pushed through the leveler main body 94. With the leveler screw 98 so disposed, the dowel pin 102 could be pressed into the leveler screw 98 to prevent rotation. The adjustment dial 100 can be buffered on the top and bottom by thrust bushings and can be operated manually, such as by application of a user's thumb to rotate the screw 98 to produce extension and retraction depending on the direction of rotation of the dial 100. While a variety of materials could be used, the bushings and the dowel pin 102 could be stainless steel, and the remaining components could be made, for instance, from aluminum or plastic.

The legs 14, 16, 18, 20, 22, and 24 can attach to or be formed with the main hinge assembly 12 by any effective arrangement. In one example of the invention, the legs 14, 16, 18, 20, and 24 could slide over a machined feature of the main hinge assembly 12 and be secured in place, such as by spot welding, mechanical fasteners, or otherwise. Likewise, the attachment assemblies 26 and 28 could have a machined feature that slides into the top of the legs 14 and 16 before being spot welded into place. Still further, the foot mount assemblies 34 and 36 could have machined features that slide into the legs 18 and 20 before being secured in place. When legs 14, 16, 18 and, 20 are secured to the main hinge assembly 12, a gap may remain in the center of the rack 10 due to an angled cut of the legs 14, 16, 18 and 20. This can be filled by a filler block 104 as seen in FIG. 6B. The filler block 104 could be of any suitable material, including an aluminum material. The filler block 104 can have a T-shaped cross section that will mate against the cut portion of the legs, such as that indicated at 20, and be secured, such as by sport welding, into place. Still further, the leveling mechanisms 38 and 40 can be engaged with or formed integrally with the distal ends of the legs 22 and 24, such as by having the legs 22 and 24 accept a machined feature of the leveler assemblies 38 and 40 to be secured, such as by spot welding, in place. Where appropriate, pockets of material can be strategically removed to reduce weight while minimizing the effects on component strength.

Some or all of the upper legs 14 and 16 and the lower anterior legs 18 and 20 could have padding to increase user comfort by thermally isolating the user from the legs 14, 16, 18, and 20 and softening the interfaces, which may be leaned on for an extended period of time. One embodiment of the invention has padding assemblies 106 comprising plastic perimeter structures with captive threads installed therein and foam secured therein or thereon. A marine vinyl or other polymeric or other material could be cut to size and wrapped around the remainder of the padding panels 106 and glued to the underside of the plastic. The padding panels 106 so formed are fastened to the legs 14, 16, 18, and 20, such as by screws passing through the legs 14, 16, 18, and 20. The vinyl covering and the padding panes 106 in general would thus be secured in place.

A material coating could be applied to allow the finish of the parts, which may be of aluminum, to remain stable through harsh environments and impact stresses. Options could include powder coating, rubberizing, enameling, spray-on liners, and other protective coatings or processes are possible. It is intended to have color options available to the user.

The bondage rack 10 could still further include a storage container, such as a soft-sided bag or a rigid box, that will closely fit the geometry of the rack 10 in the collapsed configuration of FIGS. 3A and 3B. The storage container can have wheels and a handle that may or may not telescope. This will provide portability, storability, and discretion similar to a standard suitcase. Color options will be available, and protective features may be incorporated inside of the container. A zipper or other closure can pass over three edges while allowing folding over the fourth edge to provide access the stored rack 10.

With certain details and embodiments of the present invention for a bondage rack 10 disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the inventor. Those claims shall be deemed to include equivalent constructions insofar as they do not depart from the spirit and scope of the invention. It must be further noted that a plurality of the following claims may express certain elements as means for performing a specific function, at times without the recital of structure or material. As the law demands, any such claims shall be construed to cover not only the corresponding structure and material expressly described in this specification but also all equivalents thereof.

I claim as deserving the protection of Letters Patent:

1. A collapsible bondage rack with a use configuration and a collapsed configuration, the collapsible bondage rack comprising:
   a main hinge assembly;
   an upper retaining structure retained relative to the main hinge assembly and projecting in a first longitudinal direction;
   a lower support structure retained relative to the main hinge assembly and projecting in a second longitudinal direction substantially opposite the first longitudinal direction;
   wherein the upper retaining structure and the lower support structure are relatively pivotable by operation of the main hinge assembly between the use configuration and the collapsed configuration;
   wherein the lower support structure comprises an anterior lower support and a posterior lower support, wherein the anterior lower support and the posterior lower support have proximal end portions retained relative to the main hinge assembly, wherein the anterior lower support and the posterior lower support are relatively pivotable between the use configuration wherein the anterior and posterior lower supports are spaced apart and the collapsed configuration wherein the anterior lower support and the posterior lower support are pivoted into proximity;
   wherein the upper retaining structure comprises first and second upper legs, wherein the anterior lower support of the lower support structure comprises first and second anterior lower legs, and wherein the posterior lower support of the lower support structure comprises at least one posterior lower leg;
   wherein the first and second legs of the upper retaining structure are pivotable about a lateral pivot axis relative to the first and second anterior lower legs and wherein the at least one posterior lower leg is pivotable about a lateral pivot axis relative to the first and second anterior lower legs; and
   wherein the first anterior lower leg is pivotable relative to the second anterior lower leg about a longitudinal pivot axis of the bondage rack, the longitudinal pivot axis extending substantially parallel with the first and second longitudinal directions.

2. The collapsible bondage rack of claim 1 wherein, when the collapsible bondage rack is in the use configuration, the first and second legs of the upper retaining structure project from the main hinge assembly in a first longitudinal direction and the first and second anterior lower legs of the lower support structure project from the main hinge assembly in a second longitudinal direction substantially opposite the first longitudinal direction.

3. The collapsible bondage rack of claim 2 wherein, when the collapsible bondage rack is in the use configuration, the first and second legs of the upper retaining structure project from the main hinge assembly in a substantially V-shaped configuration and the first and second anterior lower legs of the lower support structure project from the main hinge assembly in a substantially V-shaped configuration.

4. The collapsible bondage rack of claim 1 wherein, when the collapsible bondage rack is in the use configuration, the first and second upper legs project from the main hinge assembly in a substantially V-shaped configuration, the first and second anterior lower legs project from the main hinge assembly in a substantially V-shaped configuration, and wherein the at least one posterior lower leg comprises first and second posterior lower legs that project from the main hinge assembly in a substantially V-shaped configuration.

5. The collapsible bondage rack of claim 4 wherein the first and second upper legs, the first and second anterior lower legs, and the first and second posterior lower legs are disposed in a stack configuration when the bondage rack is in the collapsed configuration.

6. The collapsible bondage rack of claim 1 wherein the lateral pivot axis comprises a structural link with a first end pivotally coupled to a hinge base of the main hinge assembly and a second end pivotally coupled to a proximal portion of the upper retaining structure.

7. The collapsible bondage rack of claim 6 wherein the main hinge assembly further comprises a backing wall and wherein the structural link is limited in rotation by the backing wall when the bondage rack is in the use configuration.

8. The collapsible bondage rack of claim 7 further comprising a locking mechanism adjustable to fix the upper retaining structure against pivoting relative to the lower support structure and to permit the upper retaining structure to pivot relative to the lower support structure.

9. The collapsible bondage rack of claim 1 further comprising a first foot mount assembly retained by the first anterior lower leg spaced from a distal end of the first anterior lower leg and a second foot mount assembly retained by the second anterior lower leg spaced from a distal end of the second anterior lower leg.

10. The collapsible bondage rack of claim 9 wherein the first foot mount assembly comprises an aperture in the first anterior lower leg and wherein the second foot mount assembly comprises an aperture in the second anterior lower leg.

11. The collapsible bondage rack of claim 10 wherein each of the first and second foot mount assemblies further comprises at least one foot plate.

12. The collapsible bondage rack of claim 11 wherein each of the first and second foot mount assemblies comprises an anterior foot plate, the aperture, and a posterior foot plate.

13. The collapsible bondage rack of claim 9 further comprising first and second upper attachment assemblies retained by the upper retaining structure and first and second lower attachment assemblies retained by the lower support structure wherein the first and second lower attachment assemblies are disposed proximal to the first and second foot mount assemblies.

14. The collapsible bondage rack of claim 1 further comprising first and second upper attachment assemblies retained by the upper retaining structure and first and second lower attachment assemblies retained by the lower support structure.

15. The collapsible bondage rack of claim 14 wherein the first and second upper attachment assemblies and the first and second lower attachment assemblies comprise loops.

16. The collapsible bondage rack of claim 1 further comprising a leveling mechanism coupled to the lower support structure for stabilizing the bondage rack.

17. A collapsible bondage rack with a use configuration and a collapsed configuration, the collapsible bondage rack comprising:
   a main hinge assembly;

an upper retaining structure retained relative to the main hinge assembly wherein the upper retaining structure comprises first and second upper legs;

a lower support structure retained relative to the main hinge assembly wherein the lower support structure comprises first and second anterior lower legs and at least one posterior lower leg;

wherein, when the collapsible bondage rack is in the use configuration, the first and second legs of the upper retaining structure project from the main hinge assembly in a first longitudinal direction and the first and second anterior lower legs of the lower support structure project from the main hinge assembly in a second longitudinal direction substantially opposite the first longitudinal direction;

wherein the upper retaining structure and the lower support structure are relatively pivotable about a lateral pivot axis by operation of the main hinge assembly between the use configuration and the collapsed configuration and wherein the first and second anterior lower legs of the lower support structure are relatively pivotable about a longitudinal pivot axis by operation of the main hinge assembly between the use configuration and the collapsed configuration, the longitudinal pivot axis extending substantially parallel with the first and second longitudinal directions;

wherein the first and second anterior lower legs and the at least one posterior lower leg have proximal end portions retained relative to the main hinge assembly, wherein the first and second anterior lower legs and the at least one posterior lower leg are relatively pivotable between the use configuration wherein the first and second anterior lower legs and the at least one posterior lower leg are spaced apart and the collapsed configuration wherein the first and second anterior lower legs and the at least one posterior lower leg are pivoted into proximity.

18. The collapsible bondage rack of claim 17 wherein the first and second upper legs, the first and second anterior lower legs, and the at least one posterior lower leg are disposed in a stack configuration when the bondage rack is in the collapsed configuration.

19. The collapsible bondage rack of claim 17 further comprising a first foot mount assembly retained by the first anterior lower leg spaced from a distal end of the first anterior lower leg and a second foot mount assembly retained by the second anterior lower leg spaced from a distal end of the second anterior lower leg.

20. The collapsible bondage rack of claim 19 wherein the first foot mount assembly comprises an aperture in the first anterior lower leg and wherein the second foot mount assembly comprises an aperture in the second anterior lower leg.

21. The collapsible bondage rack of claim 20 wherein the first foot mount assembly further comprises a first foot plate wherein the first foot plate is pivotable from a use position projecting outwardly from the first anterior lower leg and a storage position substantially aligned with the first anterior lower leg substantially to close the aperture in the first anterior lower leg and wherein the second foot mount assembly further comprises a second foot plate wherein the second foot plate is pivotable from a use position projecting outwardly from the second anterior lower leg and a storage position substantially aligned with the second anterior lower leg substantially to close the aperture in the second anterior lower leg.

22. The collapsible bondage rack of claim 17 further comprising first and second upper attachment assemblies retained by the first and second upper legs and first and second lower attachment assemblies retained by the first and second anterior lower legs.

\* \* \* \* \*